United States Patent [19]

Brighton et al.

[11] Patent Number: 4,535,775

[45] Date of Patent: Aug. 20, 1985

[54] METHOD FOR TREATMENT OF NON-UNION BONE FRACTURES BY NON-INVASIVE ELECTRICAL STIMULATION

[75] Inventors: Carl T. Brighton, Malvern; Solomon R. Pollack, Dresher, both of Pa.

[73] Assignee: Biolectron, Inc., Hackensack, N.J.

[21] Appl. No.: 465,526

[22] Filed: Feb. 10, 1983

[51] Int. Cl.³ ............................................. A61N 1/36
[52] U.S. Cl. ................................................ 128/419 F
[58] Field of Search .................. 128/804, 422, 419 F, 128/82.1

[56] References Cited

U.S. PATENT DOCUMENTS

| | | | |
|---|---|---|---|
| 3,701,349 | 10/1972 | Larson | 128/82.1 |
| 3,745,995 | 7/1973 | Kraus . | |
| 3,893,462 | 7/1975 | Manning . | |
| 3,918,440 | 11/1975 | Kraus | 128/82.1 |
| 4,105,017 | 8/1978 | Ryaby et al. . | |
| 4,266,533 | 5/1981 | Ryaby et al. | 128/419 F |
| 4,285,346 | 8/1981 | Armitage | 128/804 |
| 4,315,503 | 2/1982 | Ryaby et al. | 128/82.1 |

FOREIGN PATENT DOCUMENTS 2481924 11/1981 France ............................ 128/82.1

OTHER PUBLICATIONS

"The Alternate Treatment of Fracture Non-Union" *Zimmer U.S.A. Catalogue*, Sep. 1979.
Doyle et al., "Stimulation of Bone Growth by Short Wave Diathermy" *The Journal of Bone and Joint Surgery*, vol. 45-A, No. 1, Jan. '63, pp. 15–24.
Herbst, "Electrical Stimulation of Bone Growth and Repair: A Review of Different Stimulation Methods" Text: *Electrical Stimulation of Bone Growth and Repair*, F. Burry et al., edit., Springer-Verlag Publ., Berlin & New York, 1978, pp. 1–13.

*Primary Examiner*—William E. Kamm
*Assistant Examiner*—Mitchell J. Shein
*Attorney, Agent, or Firm*—Brumbaugh, Graves, Donohue & Raymond

[57] ABSTRACT

Bone fractures previously considered incurable are healed non-invasively by applying to electrodes coupled to the skin of a living body in the vicinity of a bone fracture an alternating voltage having a wave form that is symmetrical with respect to the axis, a frequency in the range 20–100 KHz and a value in the range from about 2 to 10 volts peak to peak.

6 Claims, 1 Drawing Figure

METHOD FOR TREATMENT OF NON-UNION BONE FRACTURES BY NON-INVASIVE ELECTRICAL STIMULATION

This invention relates to a novel non-invasive method for promoting bone growth and healing in a living body by electrical stimulation. More particularly, it relates to a method of this character which is markedly effective in the treatment and cure of so-called "non-union" fractures, i.e., bone fractures that do not normally heal.

BACKGROUND OF THE INVENTION

In recent years, the response of living tissues and cells to various forms of electrical stimulation has been fairly extensively investigated. Out of this work have evolved a number of proposals for promoting the healing of bone fractures and the like, including both invasive treatments involving the use of implanted electrodes and non-invasive techniques utilizing electrostatic and electromagnetic fields.

According to one proposal disclosed in U.S. Pat. No. 3,745,995, metal splints are affixed to a broken bone by screws, and pickup coils have terminals connected both to the splints and to electrodes invasively inserted into the bone. A coil surrounding the limb having the fracture induces in the pickup coils an alternating current signal at a frequency below 1000 Hz, preferably between 1 or 10 Hz and 40 hz, and having gentle, gradual slopes, e.g., a current in the form of a sine wave or a triangular wave. Because this technique is complex and invasive in nature, it is not satisfactory.

Subsequently, U.S. Pat. No. 3,893,462 was granted to Manning for method and apparatus for promoting bone healing by stimulation with an undulating signal having a wave form whose rise time differs from its fall time, the signal being applied by electrodes in contact with the skin of a living body or by coils positioned adjacent the body. It is claimed that this produces in the body a current flow which is of greater magnitude in one direction than in the opposite direction and which enhances and speeds up the repair mechanisms with faster rates of recovery.

In another technique described in U.S. Pat. No. 4,105,017, the treatment involves subjecting living cells or tissues to pulsing electromagnetic fields generated by energizing coils with complex electrical wave forms of a specific frequency-amplitude relation.

BRIEF SUMMARY OF THE INVENTION

Contrary to what the teachings of these patents would lead one to expect, we have found that bone fractures previously considered incurable can be effectively healed by treatment with a simple alternating signal of relatively low voltage and relatively high frequency. The frequency should preferably be in the range 20-100 KHz and the wave form of the alternating voltage should preferably be symmetrical with respect to the axis. For example, it may be sinusoidal, square, or triangular in wave form. The voltage is applied to electrodes coupled to the skin of a living body in the vicinity of the bone fracture, so that the technique is non-invasive and does not injure the body being treated.

DESCRIPTION OF THE PREFERRED EMBODIMENT

Figure 1:
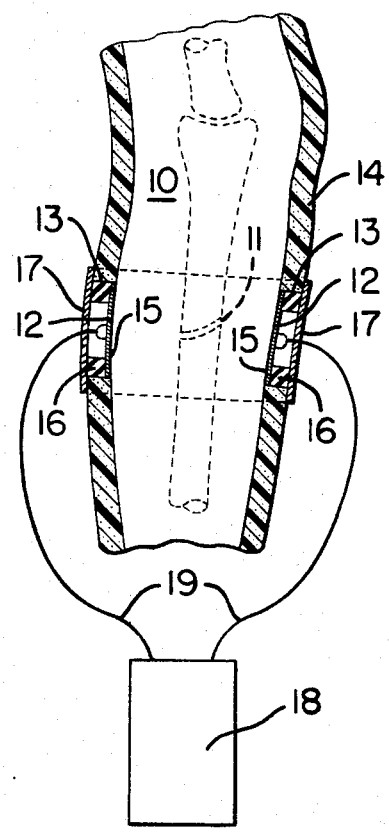

The invention may be better understood from the following detailed description of a preferred embodiment, taken in conjunction with the accompanying drawing, in which:

FIG. 1 is a schematic diagram illustrating a typical treatment of a bone fracture according to the method of the invention.

The invention will be described below as utilized in the treatment of a typical bone fracture. In FIG. 1 is shown a portion of the lower leg 10 of a person having a broken tibia at 11. According to the invention, electrodes 12 are applied to the skin of the leg 10 in the vicinity of the break 11 through ports 13 formed in the cast 14 on the leg 10. Preferably, the skin surface beneath the electrodes 12 is coated with a layer 15 of conducting jelly of any known type and ring-like bushings 16 are inserted through the ports 13 to maintain the electrodes 12 in good conducting relation with the skin. A tape or ace bandage 17 is wound around the leg 10 to hold the electrodes 12 in place.

The electrodes 12 are connected to receive a periodically varying low voltage from a suitable stimulation device 18 through the conductors 19. The conductors 19 may be of a suitable length to enable the stimulation device 18 to be carried conveniently by the patient, e.g. in a pocket or sling or secured to a belt. The stimulating device 18 is preferably of the kind disclosed in the copending application of Richard S. Dugot, Ser. No. 350,440, filed Feb. 22, 1982, for Bone Healing Apparatus, the disclosure of which is incorporated herein by reference.

The signal applied to the electrodes 12 by the source 18 may be a simple alternating voltage having a wave form that is symmetrical about the axis, a frequency in the range 20 to 100 KHz, say 60 KHz, and a value ranging from about 2 to 10 volts peak-to peak, about 5 volts peak-to-peak being preferred. The electrodes 12 may be energized either continuously or intermittently and the treatment continued for a long enough period of time to cause the fracture 11 to heal.

A group of patients, all with so-called "non-union" bone fractures, after totally unsuccessful treatment with one or more conventional procedures, were treated with the method according to the invention, with dramatic results. Surprisingly, complete healing was produced.

Each patient was put in a cast appropriate to the type of fracture in each case and the fractured bone was stimulated by alternating current at a frequency of 60 KHz continuously supplied to electrodes mounted in ports formed in the cast, as illustrated in FIG. 1. The electrodes 12 were cleaned and fresh conductive jelly applied on a daily basis and each patient was examined at monthly intervals to verify that the stimulation device was functioning properly and to ascertain the progress being made by the patient under treatment. Except for short periods when the battery was being changed, the patient was bathing or undergoing physical examination approximately monthly, the current was applied continuously.

One patient, a male aged 29, with a fracture of the left distal tibia that failed to respond to treatments over a period of about nineteen months, including the Hoffman device, bone grafts and stimulation of the kind disclosed in the aforementioned U.S. Pat. No. 4,105,017, healed completely after treatment according to the invention with a voltage of about 5 volts peak-to-peak applied to the electrodes for about 172 days.

In a second patient, a male aged 39, treatment with the method according to the invention produced complete healing of a fracture of the left distal tibia and fibula after treatment with various other known procedures over more than a year had failed. In this case, a voltage of about 5 volts was supplied continuously to the electrodes 12 for a period of about 180 days.

A third patient, a 38 year old female, had sustained a fracture of the left tibia in a train accident which refused to heal after treatment over a period of six years with a variety of conventional procedures including fixation with screws and a plate, and bone grafts. After stimulation according to the method of the invention with an alternating voltage of about 5 volts peak-to-peak at a frequency of about 60 KH continuously applied to the electrodes for a period of about 65 days, healing began to occur and continued without further stimulation until, after about another 80 days, healing of the fracture was found to be complete.

A fourth patient, a 16 year old male, who had sustained a right carpal navicular fracture from a football injury that had failed to heal after treatment including a bone graft over a period of about six months, was also treated to electrical stimulation according to the invention. A simple sine wave voltage about 5 volts peak-to-peak was applied to the electrodes for a period of about 59 days. Radiographic evaluation at the end of this period showed that the break was almost completely healed. Stimulation was discontinued and about three months later the fracture was found to be completely healed.

It will be appreciated that the invention represents a marked advance in the art in that it provides a simple, yet highly effective method for promoting the healing of non-union bone fractures that have failed to heal normally or with the aid of other conventional procedures and would otherwise be candidates for amputation.

While a stimulating current of sinusoidal wave form was used in the examples described above, any alternating current wave form that is symmetrical about the axis, e.g. square and triangular wave forms, can be used. Also, the voltage applied to the electrodes may have any value in a range from about 2 to 10 volts peak-to-peak, although about 5 volts peak-to-peak is preferred. The electrodes may be thin discs of stainless steel or other suitable material. Alternatively, they may be formed by conductive textile material incorporated in the cast next to the skin of the living body, for example. Also, each of the electrodes 12 may comprise a group of spaced apart electrodes all in contact with the skin of the living body, with each group connected to a different terminal of the source 18.

The invention is not to be limited to the specific examples described above but is susceptible of modification in form and detail within the scope of the following claims.

We claim:

1. A method for the treatment of a bone fracture in a living human body comprising the steps of disposing at least one pair of electrodes in contact with the skin of a living human body in proximity to the bone fracture, supplying to said electrodes an alternating electric signal of symmetrical waveform relative to the axis and of substantially constant amplitude, said signal having a frequency in the range from about 20 to 100 KHz and a value in the range from about two volts peak to peak to ten volts peak to peak, and continuing the application of said signal to said electrodes for a period of time sufficient to produce healing of said bone fracture.

2. A method as defined in claim 1 in which said alternating electric signal is sinusoidal in waveform.

3. A method as defined in claim 1 in which said alternating electric signal is of square waveform.

4. A method as defined in claim 1 in which said alternating electric signal is of triangular waveform.

5. A method as defined in claim 1 in which the electrical signal has a frequency of about 60 KHz and a value of about five volts peak to peak between each electrode and the skin of the living body.

6. A method as defined in claim 1 in which the bone fracture is immobilized by a cast on the living body and the electrodes are placed in contact with the skin of the body through ports formed in the cast.

* * * * *